(12) United States Patent
Chatterji

(10) Patent No.: US 7,115,284 B2
(45) Date of Patent: Oct. 3, 2006

(54) COMPOSITIONS FOR DIABETES TREATMENT AND PROPHYLAXIS

(75) Inventor: Arun K. Chatterji, Neenah, WI (US)

(73) Assignee: Ayurvedic-Life International, LLC, Neenah, WI (US)

( * ) Notice: Subject to any disclaimer, the term of this patent is extended or adjusted under 35 U.S.C. 154(b) by 295 days.

(21) Appl. No.: 10/638,811

(22) Filed: Aug. 11, 2003

(65) Prior Publication Data

US 2005/0119220 A1    Jun. 2, 2005

(51) Int. Cl.
*A01N 65/00*    (2006.01)
(52) U.S. Cl. ....................................... 424/725
(58) Field of Classification Search ................. 424/725
See application file for complete search history.

(56) References Cited

U.S. PATENT DOCUMENTS 4,481,222 A * 11/1984 Fan .............................. 426/62

FOREIGN PATENT DOCUMENTS

JP        02001103928    *   4/2001
WO       WO 95/10292    *   4/1995

* cited by examiner

*Primary Examiner*—Michael Meller
(74) *Attorney, Agent, or Firm*—Olson & Hierl, Ltd.

(57) ABSTRACT

Gurmarin containing compositions are useful for the treatment of diabetes. Glucose metabolism in a human patient is regulated by gurmarin-containing dosage forms that contain optionally a non-metabolizable polysaccharide such as the exudate of *Sterculia urens*.

2 Claims, No Drawings

COMPOSITIONS FOR DIABETES TREATMENT AND PROPHYLAXIS

FIELD OF THE INVENTION

This invention relates to the regulation of glucose metabolism in a human patient.

BACKGROUND OF THE INVENTION

The concentration of glucose in the human bloodstream must be controlled within a relatively tight range (60–120 milligrams per deciliter of blood) to maintain normal health. If blood glucose drops too low, a condition known as hypoglycemia results, with symptoms such as faintness, weakness, headache, confusion and personality changes. Severe hypoglycemia can progress to convulsions, coma and death. Excessive blood glucose, or hyperglycemia, causes excess urine production, thirst, weight loss, fatigue, and in the most severe cases, dehydration, coma and death. Chronic hyperglycemia causes tissue damage due to the chemical reactions between the excess glucose and proteins in cells, tissues, and organs. This damage is thought to cause the diabetic complications of blindness, kidney failure, impotence, atherosclerosis, and increased vulnerability to infection.

The pancreas makes hormones that regulate the concentration of glucose in the blood. Insulin lowers blood glucose levels; when glucose level rises after a meal, the pancreas secretes insulin, which causes muscle and other tissues to take up glucose from the blood stream. Glucagon raises blood glucose levels; when blood glucose levels fall, the pancreas secretes glucagon to signal the liver to make stored glucose available.

A third glucose-regulating hormone, amylin, was discovered in 1987. Physiologists now generally consider that all three hormones play a role in the complex aspects of glucose metabolism. The chemical structure of amylin and its metabolic action on muscle and pancreas tissue has recently been elucidated. Amylin is said to work with insulin to moderate the glucose-lowering effects of insulin under certain circumstances, to help replenish liver glycogen after a meal, and to encourage the synthesis of fat from excess glucose. As a result, amylin, like glucagon, can raise the blood glucose level.

Diabetes mellitus is associated with continuous and pathologically elevated blood glucose concentration; it is one of the leading causes of death in the United States and is responsible for about 5% of all mortality. Diabetes is divided into two major sub-classes: Type I, also known as juvenile diabetes, or Insulin-Dependent Diabetes Mellitus (IDDM), and Type II, also known as adult onset diabetes, or Non-Insulin-Dependent Diabetes Mellitus (NIDDM).

According to the American Diabetes Association, there are over one million juvenile diabetics in the United States. Diabetes is a form of autoimmune disease. Autoantibodies produced by the patients completely or partially destroy the insulin producing cells of the pancreas. Juvenile diabetics must, therefore, receive exogenous insulin during their lifetime. Without treatment, excessive acidosis, dehydration, kidney damage, and death may result. Even with treatment, complications such as blindness, atherosclerosis, and impotence can occur.

There are more than five million Type II (adult onset) diabetics diagnosed in the United States. Type II disease usually begins during middle age; the exact cause is unknown. In Type II diabetics, rising blood glucose levels after meals do not properly stimulate insulin production by the pancreas. Additionally, peripheral tissues are generally resistant to the effects of insulin. The resulting high blood glucose levels (hyperglycemia) can cause extensive tissue damage. Type II diabetics are often referred to as insulin resistant. They often have higher than normal plasma insulin levels (hyperinsulinomia) as the body attempts to overcome its insulin resistance. Some researchers now believe that hyperinsulinomia may be a causative factor in the development of high blood pressure, high levels of circulating low density lipo-proteins (LDLs), and lower than normal levels of the beneficial high density lipo-proteins (HDLs). While moderate insulin resistance can be compensated for in the early stages of Type II diabetes by increased insulin secretion, in advanced disease states insulin secretion is also impaired. Treatments of Type II diabetes preferably address both insulin resistance and faulty insulin secretion.

Insulin resistance and hyperinsulinomia have also been linked with two other metabolic disorders that pose considerable health risks: impaired glucose tolerance and metabolic obesity. Impaired glucose tolerance is characterized by normal glucose levels before eating, with a tendency toward elevated levels (hyperglycemia) following a meal. According to the World Health Organization, approximately 11% of the U.S. population between the ages of 20 and 74 are estimated to have impaired glucose tolerance. These individuals are considered to be at higher risk for diabetes and coronary artery disease.

Obesity may also be associated with insulin resistance. A causal linkage among obesity, impaired glucose tolerance, and Type II diabetes has been proposed, but a physiological basis has not yet been established. Some researchers believe that impaired glucose tolerance and diabetes are clinically observed and diagnosed only later in the disease process after a person has developed insulin resistance and hyperinsulinomia.

Insulin resistance is frequently associated with hypertension, coronary artery disease (arteriosclerosis), and lactic acidosis, as well as related disease states. The fundamental relationship between these disease states, and a method of treatment, has not been established.

Insulin and sulfonylureas (oral hypoglycemia therapeutic agents) are the two major classes of diabetes medicines prescribed today in the United States. Insulin is prescribed for both Type I and Type II diabetes, while sulfonylureas are usually prescribed for Type II diabetics only. Sulfonylureas stimulate natural insulin secretion and reduce insulin resistance; these compounds do not replace the function of insulin in metabolism. Approximately one-third of patients who receive sulfonylurea become resistant to it. Some Type II diabetics do not respond to sulonylurea therapy. Of patients who do respond to initial treatment with sulfonylureas, 5–10% are likely to experience a loss of sulfonylurea effectiveness after about ten years.

Insulin itself has a relatively narrow therapeutic window. Relatively high insulin doses can produce hypoglycemic shock as the blood glucose drops too low. Low or infrequent doses may result in hyperglycemia.

In Europe, two other classes of oral hypoglycemic agents are available, i.e., biguanides and alpha-glucosidase inhibitors. Biguanides work by reducing glucose production in the liver and limiting glucose absorption. Although biguanides are also used in Canada, they are banned in the U.S. due to increased incidence of mortality. Alpha-glucosidase inhibitors are sold in certain European countries, but have not obtained FDA approval for use in the U.S. These drugs reduce high blood glucose levels by slowing the uptake of ingested foods. Side effects include flatulence, diarrhea, and abdominal pain.

U.S. Pat. No. 4,761,286 to Hiji discloses that an aqueous extract derived from the leaves of *Gymnema sylvestre* can be utilized in combination with a foodstuff that is absorbed as glucose by the intestinal tract so as to inhibit glucose absorption. Chatterji, International Patent Application No. WO 95/10292, reported that glucose metabolism in a human patient can be effectively modulated by oral administration of an extract derived from the leaves of *G. sylvestre* in combination with a bio-inert polysaccharide, i.e., a polysaccharide that is non-metabolizable by the patient. Heretofore the inhibitory action on the absorption of sugar in the intestinal tract by *G. Sylvestre* extracts has been attributed to gymnemic acid and the varius derivatives thereof present. See, for example, U.S. Pat. No. 5,137,921 to Kensho et al. and Shimizu et al., J. Vet. Med. Sci. 59(4):245–251 (1997).

It has now been found, however, that glucose metabolism in a human patient can be effectively modulated by oral administration of gurmarin, a polypeptide; optionally in combination with a non-metabolizable polysaccharide.

SUMMARY OF THE INVENTION

This invention is directed to compositions and methods for modulating glucose metabolism in a mammal, such as a human patient.

In one aspect, the present invention provides a relatively high molecular weight (HMW), gurmarin-containing isolate that can be derived from the leaves of a herb belonging to the plant family Asclepiadaceae, genus *Gymnema*, that contains gurmarin, a 35 amino acid residue polypeptide. The present invention also includes therapeutic dosage forms containing gurmarin and pharmaceutically acceptable carrier therefor. Gurmarin can be administered alone or together with a non-metabolizable polysaccharide, preferably a *Sterculia urens* exudate, preferably in a respective weight ratio in the range of about 1:50 to about 1:5, more preferably about 1:25.

The aforementioned isolate containing gurmarin is readily obtainable by aqueous or aqueous ethanolic extraction of the leaves of the species *Gymnema sylvestre*, followed by isolation of a relatively high molecular weight insulinotropically active principle from the extract. The isolated, insulinotropically active principle contains gurmarin, having a molecular size of about 4000 Daltons.

Another aspect of the present invention is a method for modulating glucose metabolism in a mammal, e.g. a human patient, a household pet, and the like, by orally administering to the mammal an effective amount of isolated gurmarin or of the aforesaid combination of ingredients which is sufficient to at least stabilize, and preferably reduce, the blood glucose level of the mammal such as a human patient.

The present compositions are useful as a dietary supplement, to delay the onset of diabetes, as an adjunct therapy with insulin for Type I diabetic patients to assist in blood sugar level control, and to reduce the likelihood of the onset of diabetes in those who are genetically predisposed to diabetes, cholesterolemia or obesity. The isolate of the present invention is also useful for the treatment of diabetic retinopathy.

DESCRIPTION OF PREFERRED EMBODIMENTS

Gurmarin is a 35 amino acid residue polypeptide that includes three intramolecular disulfide bonds and has a molecular weight of about 4000 Daltons. Gurmarin can be obtained by chemical synthesis, and also by extraction from the leaves of a plant from the genus *Gymnema* (family Asclepiadaceae) such as *G. sylvestre, G. inodorum*, and the like. The structure of gurmarin can be represented by the formula

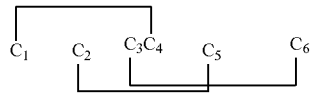

wherein the amino terminus is to the left and the three disulfide bonds that are present are denoted by $C_1$–$C_4$, $C_2$–$C_5$, and $C_3$–$C_6$, respectively. Stated in another way, the disulfide bonds are present between the cysteine residues at positions 3 and 18; 10 and 23; and 17 and 33. In the foregoing formula the standard one-letter amino acid residue abbreviations have been used where

| Amino acid | Three-letter abbreviation | One-letter abbreviation |
|---|---|---|
| alanine | Ala | A |
| arginine | Arg | R |
| asparagine | Asn | N |
| aspartic acid | Asp | D |
| cysteine | Cys | C |
| glutamic acid | Glu | E |
| glutamine | Gln | Q |
| glycine | Gly | G |
| histidine | His | H |
| isoleucine | Ile | I |
| leucine | Leu | L |
| lysine | Lys | K |
| methionine | Met | M |
| phenylalanine | Phe | F |
| proline | Pro | P |
| serine | Ser | S |
| threonine | Thr | T |
| tryptophan | Trp | W |
| tyrosine | Tyr | Y |
| valine | Val | V |

Gurmarin has been reported as suppressing the response of the rat chorda tympani nerve to sweet taste stimuli such as glucose, sucrose, glycine and saccharine, but as having no apparent effect in humans. Fletcher et al., Eur. J. Biochem. 264:525–533 (1999). It has now been found, however, that gurmarin has insulinotropic properties and is useful for modulation of glucose metabolism in human patents alone, or in conjunction with a non-metabolizable polysaccharide such as *Sterculia urens*.

A convenient source of gurmarin is *Gymnema sylvestre*, a plant that belongs to the family Asclepiadaceae. The plant grows principally in Central and Western India, in tropical Africa and in Australia. It has been reported that the raw leaves of *G. sylvestre* have been used in India as a folk medicine for various afflictions including diabetes mellitus. Some fourteen or fifteen different compounds, all having a relatively lower molecular weight, are reported to have been isolated from the leaves of *G. sylvestre* by various techniques (see, e.g., Stocklin, J. Agr. Food Chem., 1969, 17(4):704–708 and Sinsheimer, J. Pharm. Sci., 1970, 59(5): 622–628). U.S. Pat. No. 5,137,921 reports that Conduritol A, a low molecular weight monosaccharide (M.W. 146) isolated from plants such as *Marsdenia condurango* and *Gymnema sylvestre*, is an active anti-diabetic agent.

Another possible source of gurmarin is *G. inodorum* leaf extract. *G. inodorum* is liana plant that grows wild in Southwest Asia. Other *Gymnema* species are *G. lignosum, G. pachyglossum, G. stenophyllum*.

Gurmarin can be obtained from a water extract or an aqueous alcoholic extract of fresh *G. sylvestre* leaves by size selective filtration of the extract to isolate selected molecular weight, insulinotropically active fractions therefrom. In one preferred embodiment, the obtained isolate having a molecular weight of at least about 3000 Daltons, as determined by molecular weight cut-off (MWCO) filtration, contains gurmarin and is illustrative of a gurmarin isolate suitable for practicing the present invention.

Preferably an extract is obtained by extraction of *G. sylvestre* leaves with a monohydric C1 to C4 alcohol, e.g., ethanol, isopropanol, and the like, most preferably aqueous ethanol. The insulinotropically active portion of the *G. sylvestre* extract is then isolated by molecular weight cut-off filtration. In particular, the active portion is isolated by filtration of an aqueous solution of the extract through a membrane having a molecular weight cut-off of about 3000 Daltons, and the material retained by the membrane (i.e., the retentate), which has a molecular weight of at least about 3000 Daltons, is collected and isolated.

The gurmarin containing product of the present invention is preferably prepared by soaking fresh leaves of *G. sylvestre* for at least about 4 hours at ambient temperature in an aqueous alcoholic solution, preferably an aqueous ethanolic solution containing about 40 volume percent of ethanol. If water is used as the sole extraction medium, the temperature is somewhat higher, e.g., about 35 to about 85° C.

In a preferred embodiment, the leaves are soaked in water for about 4 to 24 hours, preferably about 18 hours, and then ethanol is added to the water to obtain an ethanol concentration of at least about 40% by volume, and the soaking is continued in the resulting aqueous ethanol solution for at least about 4 hours thereafter. The resulting liquid extract is filtered to remove extraneous solids and distilled to drive off ethanol and produce an aqueous bottoms solution, which is then treated with sulfuric acid to lower the pH thereof to a value of no more than about 2 and to precipitate out acid-insoluble salts that had been produced. The precipitates are removed by filtration, and the filtrate is neutralized with sodium hydroxide. The neutralized extract is then concentrated, and purified to produce a gurmarin containing isolate (the "isolate").

This isolate is then preferably lyophilized to enhance storage life and combined with a pharmaceutically acceptable carrier for oral administration. Optionally, the isolate is combined with a non-metabolizable polysaccharide such as *Sterculia urens* exudate, or a hydroxypropylmethylcellulose (HPMC), to produce an oral dosage form that contains gurmarin. As used herein and in the appended claims, the term "non-metabolizable polysaccharide" refers to a polysaccharide that is not significantly metabolized by a human patient. Also suitable for the present purposes as a non-metabolizable polysaccharide are the partially esterified oligosaccharides and polysaccharides disclosed in U.S. Pat. No. 4,959,466 to White. Illustrative are polysaccharides include, for example, xanthan gum, guar gum, gum arabic, the alginates, hydroxypropyl cellulose, cellulose hydrolysis products, starch hydrolysis products, karaya gum, and the like. Preferably, the non-metabolizable polysaccharide is the dried exudate of the tree *S. urens*, found in India, and readily available commercially.

In a preferred embodiment, the gurmarin-containing isolate is preferably lyophilized and combined with the non-metabolizable polysaccharide in a weight ratio in the range of about 2:1 to about 1:2, respectively, to provide a gurmarin-to-polysaccharide weight ratio in the range of about 1:50 to about 1:5, more preferably about 1:25. The resulting combination can then be filled into hard gelatin capsules for oral administration with or without excipients. A typical gelatin capsule embodying the present invention contains about 100 to about 200 milligrams of the lyophilized gurmarin-containing isolate and about 150 to about 300 milligrams of *S. urens* exudate.

The dosage and therapeutically effective amount to be administered to a human patient for modulating glucose metabolism of the patient will vary depending upon, inter alia, the age, weight and condition of the patient. The usual daily dosage is preferably in the range of about 200 milligrams to about 900 milligrams of the gurmarin-containing lyophilized isolate per day, preferably in conjunction with about 300 milligrams to about 1350 milligrams of non-metabolizable polysaccharide such as *S. urens* exudate.

As used herein, the term "therapeutically effective amount" means that amount of the isolate that will elicit the biological or medical response of a patient that is being sought by a clinician.

The term "pharmaceutically acceptable carrier" as used herein means a non-toxic, inert solid, semi-solid or liquid filler, diluent, encapsulating material or formulation auxiliary of any type.

A preferred schedule of administration using capsules containing about 100 milligrams of the lyophilized isolate and about 150 milligrams *S. urens* exudate is provided in Table 1, below.

TABLE 1

Dosage Schedules

| Patient diagnosis | Dosage Schedule* |
| --- | --- |
| Hyperinsulinemia | 1–2 capsules b.i.d. |
| Type II diabetic (moderate) | 2 capsules b.i.d. |
| Type II diabetic (high) | 2–3 capsules t.i.d. |
| Type I diabetic (moderate) | 1 capsule b.i.d. |
| Type I diabetic (high) with insulin as adjunct therapy | 2 capsules t.i.d. |

*b.i.d. = 2 times per day; t.i.d. = 3 times per day

The present oral dosage forms are eminently well suited as prophylactics for patients genetically pre-disposed toward diabetes, cholesterolemia or obesity.

The dosage regimen for the present, gurmarin-containing compositions is based on a variety of factors, including the type, age, weight, sex and medical condition of the patient, the severity of condition, and the like.

For example, expectant mothers identified as likely to be so pre-disposed on the basis of family history, can take oral doses of the aforedescribed lyophilized isolate throughout the full terms of their respective pregnancies. The likelihood of elevated blood sugar levels for the mothers and their newborn babies is greatly minimized in this manner. For expectant mothers, the preferred oral dosage is about 200 milligrams of the lyophilized isolate together with about 300 milligrams of *S. urens* exudate twice daily, i.e., a 500 milligram capsule, b.i.d., containing the lyophilized isolate of the present invention and the *S. urens* exudate in a respective weight ratio of about 2:3. The isolate of the present invention is also useful for the treatment of diabetic retinopathy.

The gurmarin containing isolate of the present invention can be evaluated for insulinotropic activity by a variety of procedures, well known in the art. For example, insulin producing cells can be treated with the isolate of the present invention and the insulin production of the cells can be monitored by the double antibody method of Morgan et al., Diabetes 12:115–126 (1963), the relevant disclosure of which is incorporated herein by reference. Rat insulinoma (RIN) cells are a convenient model for studying effects of pharmaceutical agents, such as the isolate of the present invention, on mammalian insulin production. RIN cells can be cultured in a glucose rich medium such as Dulbecco's Modified Eagle's Medium (D-MEM), which contains glucose (typically about 0.1 to about 0.5% by weight) and about 10% by weight of fetal calf serum (FCS), and which provides nutrients such as glucose, amino acids, and vitamins suitable for mammalian cell metabolism.

The present invention is further illustrated by the following non-limiting examples.

EXAMPLE 1

Preparation of Extract and Isolate

Fresh leaves of *Gymnema sylvestre* were purchased and identified by a botanist. The fresh leaves were soaked for about 18 hours in tap water (about 1 kg leaves/4 L tap water) at ambient temperature. Aqueous ethyl alcohol (about 90 volume percent ethanol) was added thereto in sufficient quantity to bring the net alcohol percent level to about 40% by volume, and the entire batch was distributed with stirring into ten Erlenmeyer flasks. Flasks were placed on a shaker table and shaken for about four hours.

The flask contents were filtered and the recovered liquid extract was distilled in several batches to remove ethyl alcohol. The obtained aqueous bottoms solutions were combined, and dilute sulfuric acid (about 1 to 2 molar) was added thereto to reach a final pH of about 2. A sludge composed of acid-insoluble salts was formed and was removed by filtration. Soluble salts of sodium and potassium, inherent from the leaves, remained in the filtrate. The filtrate was neutralized with dilute sodium hydroxide and deionized by passing through an ion exchange column. The resulting solution (eluate) was concentrated to a semi-solid light-brown mass (a "syrupy" mass the consistency of molasses) using a rotary flask equipped with a vacuum, with the rotary flask rotated at a 45 degree angle on a water bath heated to a temperature of about 55–70° C.

The semi-solid concentrate was then subjected to ultrafiltration using stirred Amicon filtration cells and molecular weight cut-off (MWCO) membranes. In particular, the obtained semi-solid concentrate was fractionated using 200 mL Amicon stirred ultrafiltration cells (Millipore Catalog No. 5123) and matching 3000 MWCO membranes (Millipore Catalog No. PLBC 06210) to obtain a permeate fraction having a molecular weight less than about 3000 Daltons and a retentate fraction (the isolate) having a molecular weight of at least about 3000 Daltons.

EXAMPLE 2

Bioassay of *Gymnema sylvestre* Isolate

The insulin-releasing activity of the obtained permeate and retentate of Example 1 were tested by radioimmunoassay (RIA) using an RIA kit (Catalog No. RI-13K) purchased from Linco Research, Inc., St. Louis, Mo., utilizing rat insulinoma (RIN-58) cells, I-125 labeled insulin, rat insulin antiserum, and the double antibody technique of Morgan et al., *Diabetes* 12:115–126 (1963). The main activity was found in the retentate, which has a MWCO of at least about 3000 Daltons.

Rat insulinoma cells (RIN-58) were plated in 6-well plates and grown in a tissue culture medium that contained glucose. At 80% confluence, the medium was replaced with a glucose-free medium. About 24 hours later, fresh serum-free medium containing 10 mM glucose was added along with the fraction to be assayed. The cells were incubated for 3 hours. Duplicate aliquots of 25 μL each were drawn from the wells for RIA. The assay results are reported in Table 2, below.

TABLE 2

Bioassay of Insulin-Releasing Activity

| Fraction | Activity |
|---|---|
| Retentate (MW ≧ 3000 Daltons) | 9.5 ng/mL |
| Permeate (MW < 3000 Daltons) | 2.35 ng/mL |

EXAMPLE 3

Assay for Gurmarin

A lyophilized isolate of Example 1 was dissolved in TRIS-buffered water (Tris/Tris HCl; pH about 8.2) and placed in about 1 milliliter of Coomassie® Reagent solution contained in a 10-milliliter vial. The sample exhibited a color change from brown to blue at 4° C. This color change indicates the presence of a polypeptide or protein.

The development of color in Coomassie® dye-based protein and polypeptide assays is believed to be associated with the presence of certain basic amino acid residues (primarily arginine (R), lysine (K) and histidine (H)). In general, the mass of a protein or peptide must be at least 3,000 Daltons to be assayed in this manner.

EXAMPLE 4

Elemental Analysis

A lyophilized isolate of Example 1 was analyzed for the presence of sulfur, carbon, hydrogen, and nitrogen. The analytical results are set forth below:

| | |
|---|---|
| sulfur | 0.14 wt.-% |
| carbon | 21.67 wt.-% |
| hydrogen | 5.37 wt.-% |
| nitrogen | 6.19 wt.-% |

EXAMPLE 5

Quantitative Assay for Polypeptide

A lyophilized isolate of Example 1 was dissolved in TRIS-buffered water (Tris/Tris HCl) and subjected to the Coomassie® Protein assay using a Coomassie® Protein Assay Kit 23200 (Pierce, Rockford, Ill.) and bovine serum albumin (BSA) as the standard protein against which to measure the concentration. The standards were made using aqueous 40% ethanol as the diluent. The Coomassie® Reagent was equilibrated at room temperature for all samples and standards.

Each standard (0.1 ml) of an established concentration was placed in a 20-milliliter vial and Coomassie® Reagent (5 ml) was added thereto. Each sample was prepared in a similar manner. The vials were then incubated for 10 minutes at room temperature.

Measurements were made on a Varian Cary 5000 double beam UV-Vis-NIR spectrophotometer. Each sample was stirred before being placed in a polystyrene cuvette. The blank for determining the UV-Vis baseline was aqueous 40% ethanol.

An absorbance value at 595 nanometers was determined, and a plot of the noted absorbance value @595 nm vs. BSA concentration in µg/ml (concentration curve) was prepared. Any obvious outliers were removed from the plot and a best fit linear regression was applied. The resulting line equation $Y=MX+B$ and $R^2$ linearity values (Y=Absorbance @595 nm; X=concentration in µg/ml) were found to be $Y=0.001X+0.5174$, $R^2=0.9974$. The polypeptide concentration was determined from the plot and back calculated from the concentration curve to determine the amount of polypeptide present. The experimental results are presented below:

| Amount of Sample | Calculated wt.-% Polypeptide |
|---|---|
| 0.01231 g/2 ml | 3.3 |

These experimental results confirm the presence of a sulfur-containing polypeptide in the lyophilized isolate, i.e., the retentate fraction having a molecular weight of at least about 3000.

The foregoing discussion and the examples are intended as illustrative of the present invention and are not to be taken as limiting. Still other variations within the spirit and scope of the present invention are possible and will readily present themselves to those skilled in the art.

I claim:

1. A therapeutic dosage form useful for treatment of diabetes comprising an insulinotropically effective amount of isolated gurmarin and a non-metabolizable polysaccharide, which is *Sterculia urens* exudate, wherein said gurmarin and the polysaccharide are present in the dosage form in a respective weight ratio in a range of about 1:50 to about 1:5.

2. A therapeutic dosage form in accordance with claim 1 wherein gurmarin and the polysaccharide are present in the dosage form in a respective weight ratio of about 1.25.

* * * * *

UNITED STATES PATENT AND TRADEMARK OFFICE
CERTIFICATE OF CORRECTION

| | |
|---|---|
| PATENT NO. | : 7,115,284 B2 |
| APPLICATION NO. | : 10/638811 |
| DATED | : October 3, 2006 |
| INVENTOR(S) | : Arun K. Chatterji |

It is certified that error appears in the above-identified patent and that said Letters Patent is hereby corrected as shown below:

Column 4,
Lines 8-13, the formula should be depicted as follows:

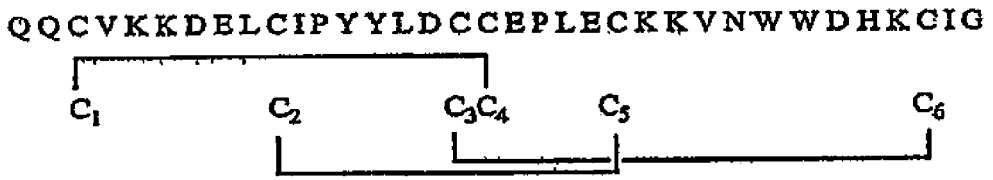

Column 8,
Line 22, "(MW ≧ 3000 Daltons)" should be -- (MW ≥ 3000 Daltons) --.

Column 10,
Line 27, "1.25" should be -- 1:25 --.

Signed and Sealed this

Twentieth Day of March, 2007

JON W. DUDAS
*Director of the United States Patent and Trademark Office*